(12) United States Patent
Kamradt et al.

(10) Patent No.: US 9,020,155 B2
(45) Date of Patent: Apr. 28, 2015

(54) ELECTROLARYNX

(75) Inventors: Brian Kamradt, Indianapolis, IN (US); Bradley Allen Wheeler, Greenwood, IN (US)

(73) Assignee: Engineered Medical Systems, Inc., Indianapolis, IN (US)

( * ) Notice: Subject to any disclaimer, the term of this patent is extended or adjusted under 35 U.S.C. 154(b) by 354 days.

(21) Appl. No.: 13/619,030

(22) Filed: Sep. 14, 2012

(65) Prior Publication Data
US 2014/0079233 A1    Mar. 20, 2014

(51) Int. Cl.
*A61F 2/20*    (2006.01)

(52) U.S. Cl.
CPC .............. *A61F 2/20* (2013.01); *A61F 2002/206* (2013.01)

(58) Field of Classification Search
None
See application file for complete search history.

(56) References Cited

U.S. PATENT DOCUMENTS

| | | | |
|---|---|---|---|
| 3,766,318 A | 10/1973 | Webb | |
| 3,978,286 A | 8/1976 | Watson | |
| 4,272,647 A | 6/1981 | Veit | |
| 7,212,639 B1 | 5/2007 | Houston | |
| 2003/0031326 A1* | 2/2003 | Lukacovic | 381/70 |

\* cited by examiner

*Primary Examiner* — Regina N Holder
(74) *Attorney, Agent, or Firm* — Swanson & Bratschun, L.L.C.

(57) ABSTRACT

An electrolarynx includes a motor having a locating diaphragm, a bobbin, and a magnetic assembly. The bobbin includes a striker and coil wires wound about a coil cylinder of an electromagnet. The locating diaphragm maintains the position of the bobbin along the longitudinal axis of the housing. The magnetic assembly includes a magnet and a non-magnetic guide disc that sandwiches the magnet to the housing. The magnet and the coil wires drive the striker and, in turn, a contact diaphragm in the cap of the electrolarynx that makes contact with a patient's throat to produce vibrations similar to those produced by the larynx. To avoid "gravitational wear" of the coil wires against a magnetic cup used to center the coil wires, the walls of the cup are made thinner and the magnetic cup may be replaced with a non-magnetic cup or the magnetic cup is removed altogether.

19 Claims, 4 Drawing Sheets

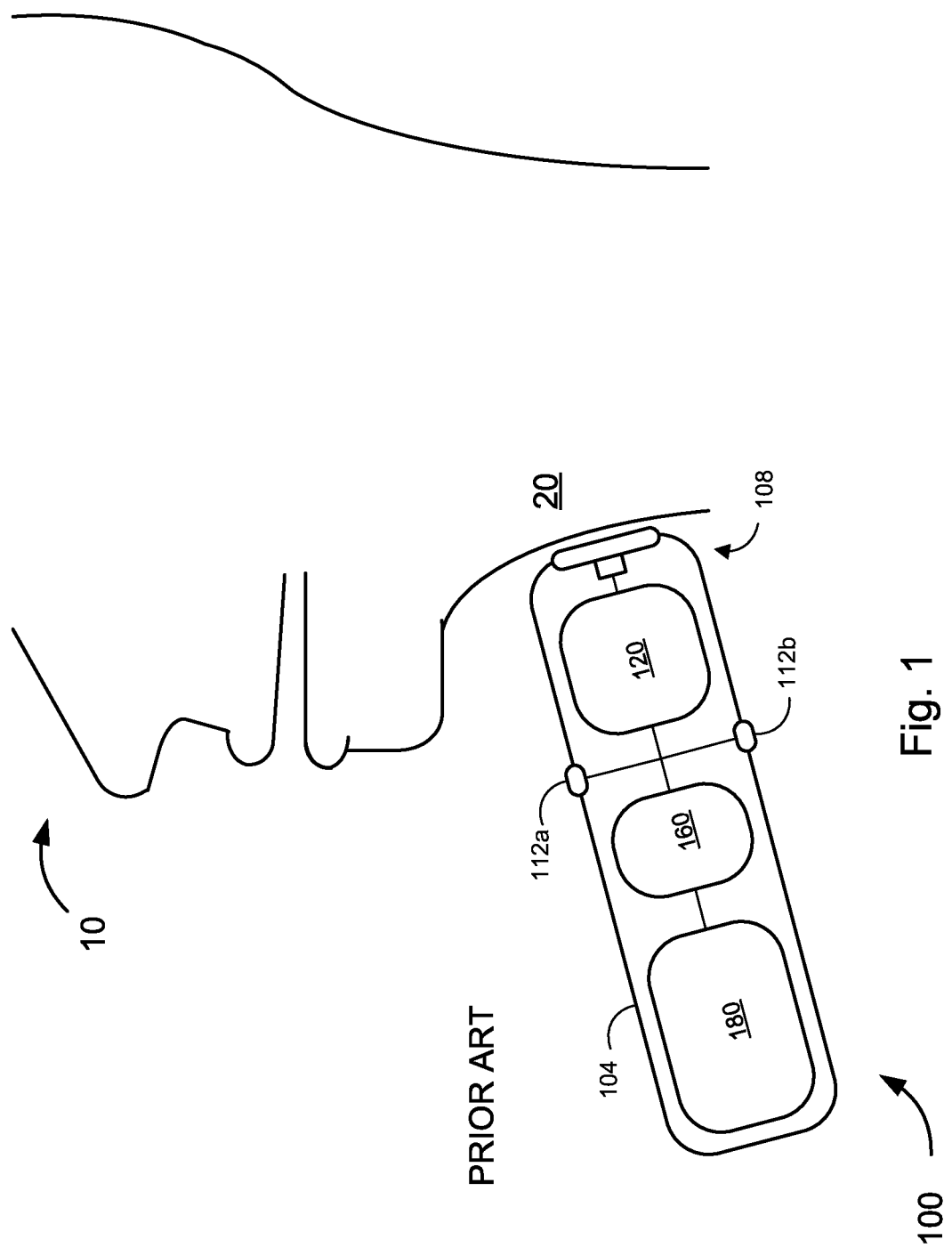
Fig. 1
PRIOR ART

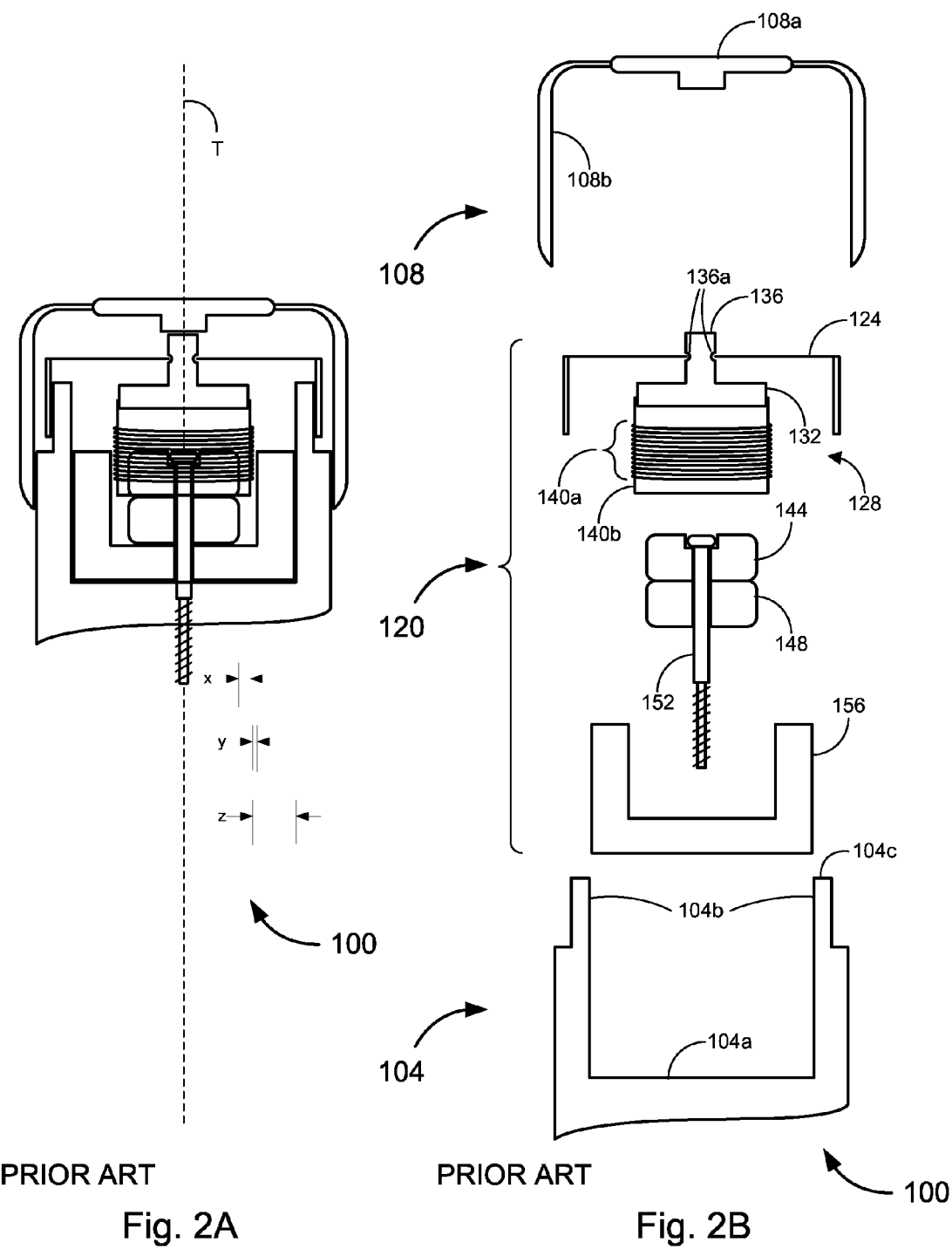
PRIOR ART
Fig. 2A
PRIOR ART
Fig. 2B

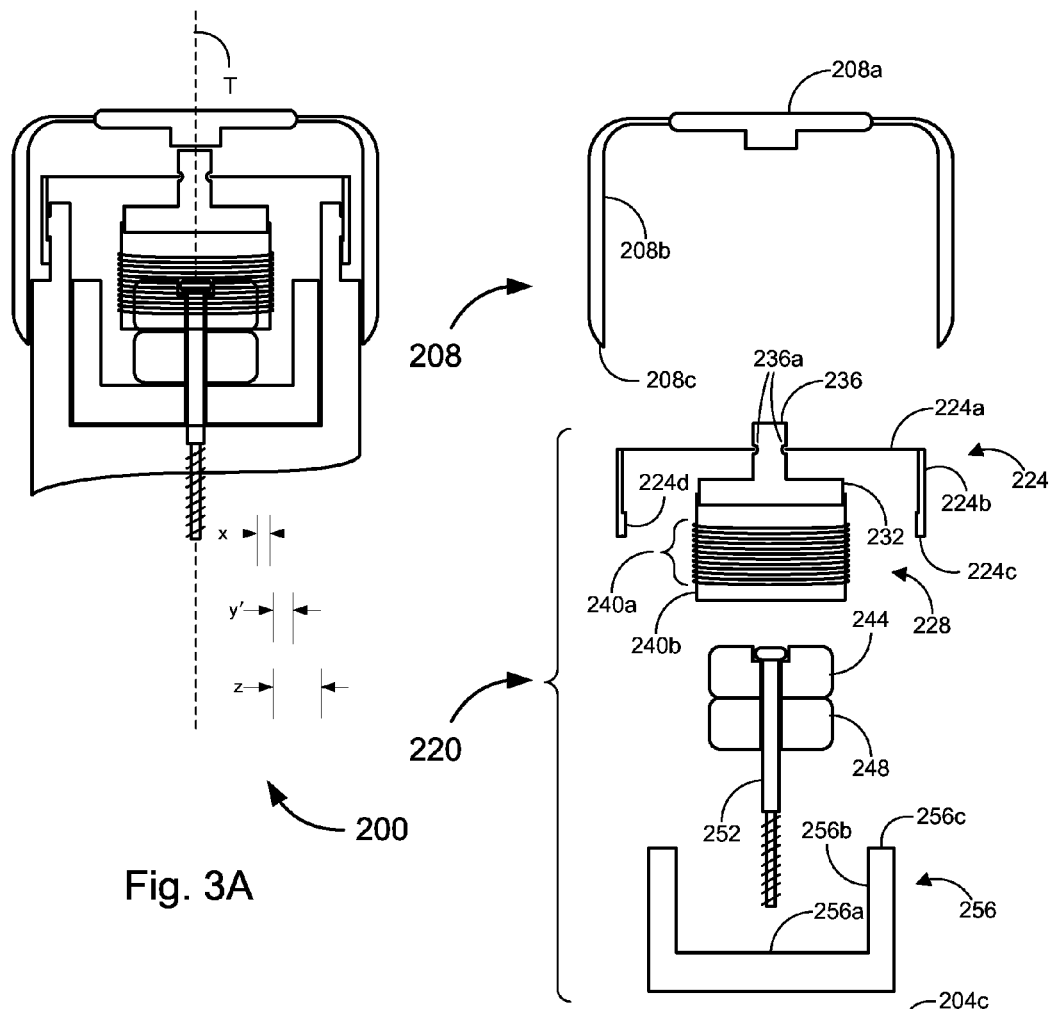
Fig. 3A
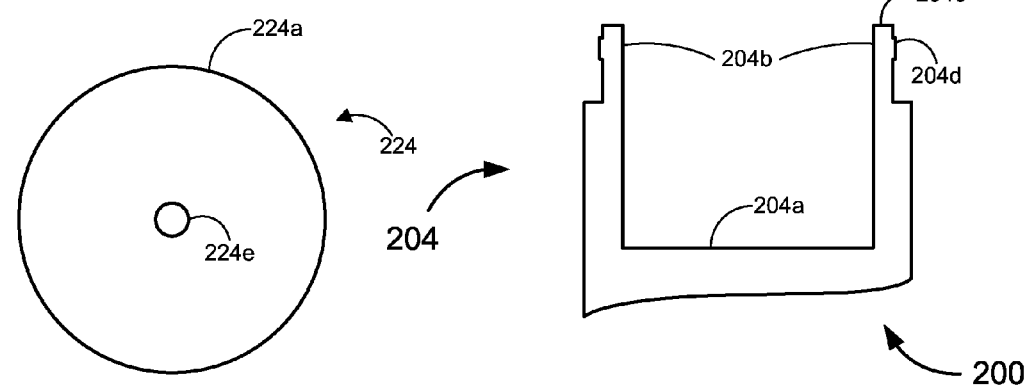
Fig. 3C
Fig. 3B

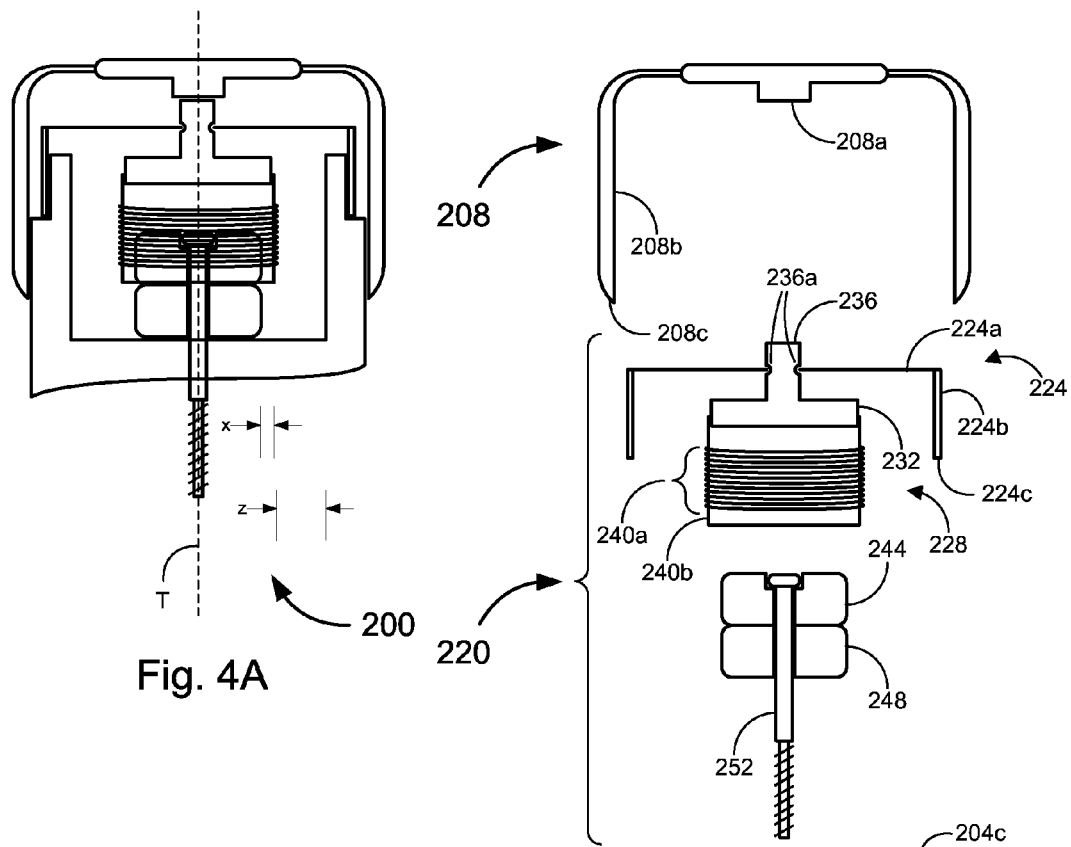
Fig. 4A
Fig. 4B
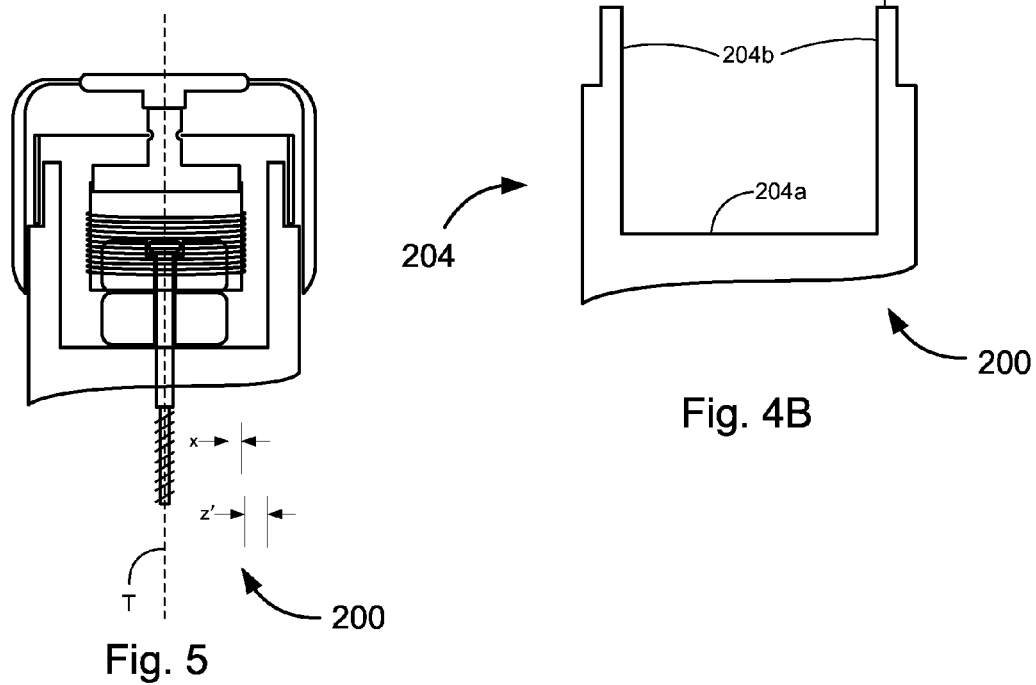
Fig. 5

ELECTROLARYNX

TECHNICAL FIELD

The present disclosure is directed toward an apparatus—herein referred to as an "electrolarynx" or "electro-larynx"—that reproduces the role of the larynx in speech patients who have experienced cancer or other conditions that necessitate the removal of the larynx. A method for extending the life of an electrolarynx is also described.

BACKGROUND

For many people who have lost their larynx due to cancer or other conditions requiring the removal of the larynx (i.e., "laryngectomee" patients), regaining speech is possible only through the use of an artificial larynx. The earliest artificial larynx dates back to around the 1920s, with electric versions appearing in the 1940s. These devices can make a huge difference in the lives of people who have had their voice boxes removed. Today, many regions provide such devices free of charge to patients, along with maintenance and training in how to use them.

One of the most common types of electrolarynxes is a hand-held device which is held against the throat and turned on when the person wants to speak, as shown, e.g., in FIG. 1, where an electrolarynx 100 is held against throat 20 of patient 10. The electrolarynx produces vibrations which are similar to those generated by the vocal cords, allowing the person to speak relatively normally. It is also possible to use an internal electrolarynx, which vibrates an inserted tube.

Learning to use an electrolarynx can take time. After surgery, patients often have scarring or other damage in their throats which may require them to move the electrolarynx around along their throat in order to find the best spot to use the device (sometimes referred to as a "sweet spot"). When well-positioned, the electrolarynx will allow people to speak relatively normally, although speech can have a slightly flattened, mechanical sound. Some people also find that the "sweet spot" changes with time, requiring small adjustments to the position of the device. Many patients like to use an external electrolarynx because it requires minimal maintenance, and if one device does not work, it is easy to replace it and work with another one.

In prior electrolarynxes, such as that shown in FIGS. 2A and 2B, a magnetic housing (typically embodied as a magnetic cup) is generally used in order to center the voice coil or coil wires. By centering the voice coil, a clear tone may be produced and amplified from the voice coil, which floats in the magnetic housing.

An issue with such prior art electrolarynxes is that these devices are turned on and off constantly, which results in wear and damage to the wires of the voice coil when the voice coil rubs against the magnetic housing while under the pull of gravity (hereinafter referred to as "gravitational wear"), such as when the device is left lying on its side (or along its axis) or when the device is held against the throat (e.g., as shown in FIG. 1) while in the off-state between sentences.

In addition, in prior art electrolarynxes, such as that shown in FIGS. 2A and 2B, the radial distance (i.e., extending from the T-axis) between the coil wires 140a and the inner diameter of magnetic cup 156 (denoted by distance "y" in FIG. 2A; hereinafter, "coil-cup gap" or "cup gap") is less than the radial distance between the outer diameter of guide disc 144 and the inner diameter of coil cylinder 140b (denoted by distance "x"; hereinafter, "guide disc gap"). Such a configuration also contributes to gravitational wear of the coil wires.

In use, the coil wires produce an electromagnetic field driving a striker, which in turn perturbs a contact diaphragm so as to produce vibrations that simulate those generated by the vocal cords. Gravitational wear on the voice coils or coil wires may disrupt the electromagnetic field which diminishes or destroys the functionality of the electrolarynx, thus further diminishing the speech capabilities of the patients who have already lost their natural ability to speak.

The present invention is directed toward overcoming one or more of the problems discussed above.

SUMMARY OF THE EMBODIMENTS

An apparatus for simulating the larynx (i.e., an electrolarynx) is described. An aspect of the electrolarynx includes a waveform generator and a transducer (or motor). The waveform generator is configured to generate an input signal of a select frequency. The transducer includes a housing, a striker, a bobbin, a magnet, and a guide disc. The housing extends along a housing axis, while the striker is confined for movement along the housing axis.

The bobbin comprises a support plate, which extends radially from the housing axis, and a coil cylinder, which extends axially from the support plate opposite the striker. The striker is attached to the support plate at the housing axis. The coil cylinder is wrapped with a coiled wire that is electrically coupled to the waveform generator to create an electromagnetic field. The magnet is mounted within the housing, sandwiched between the guide disc and the housing. The magnet is configured to interact with the electromagnetic field. In use, the bobbin (along with the striker) moves along the housing axis as a result of the waveform-generated electromagnetic field. As a result, the guide disc is telescopingly received within the coil cylinder. Here, telescopingly received refers to the coil cylinder and the guide disc being in relative motion with each other along the housing axis when in use, similar to sections of a collapsing telescope being in relative motion with each other along the telescope's axis when the telescope is either extended or collapsed.

An outer surface of the coiled wire is a uniform first distance from an inner surface of the housing in use, and this uniform first distance defines a housing gap. An outer surface of the guide disc is a uniform second distance from an inner surface of the coil cylinder, and this uniform second distance defines a guide disc gap. The housing gap is configured to be greater than the guide disc gap. In some embodiments, the housing gap is at least 0.015 inch.

According to some embodiments, the transducer further includes a locating diaphragm, which may be made of rubber. In some embodiments, the locating diaphragm has a recess that fits about a circumferential groove that is at a predetermined position along the longitudinal length of the striker, so as to confine the movement of the striker along the housing axis.

In another aspect, the electrolarynx further includes a cup-shaped magnetic housing located within the housing, where the cup sidewalls of the magnetic housing are configured to surround at least a portion of the guide disc when in use. The magnetic housing may include either a magnetic cup or a non-magnetic cup. An inner diameter of the cup sidewalls have a uniform third distance from the outer surface of the guide disc that defines a cup gap, and the cup gap is configured to be greater than the guide disc gap. In some embodiments, the cup gap is at least 0.015 inch.

A method is described for extending the life of an electrolarynx, such as one of the electrolarynxes above. A first aspect of the method includes providing one of the electrolarynxes above (one without the cup-shape magnetic housing), and providing a housing gap greater than a guide disc gap. In some embodiments, the housing gap is provided that is at least 0.015 inch. A locating diaphragm may also be provided to confine the striker to movement along the housing axis.

A second aspect of the method includes providing one of the electrolarynxes above (one having the cup-shaped magnetic housing), and providing a cup gap greater than the guide disc gap. In some embodiments, the cup gap is provided that is at least 0.015 inch.

The apparatuses for simulating the larynx (i.e., the electrolarynxes) as described herein allow for several ways in which to avoid gravitational wear (see, e.g., the methods above for extending the life of an electrolarynx), and thus prolong the operational life of the electrolarynx. The advantages of reclaimed speech for laryngectomee patients may be prolonged in an efficient, inexpensive, and less complex manner. Some embodiments allow for a less obtrusive device, which allows patients to become more comfortable in speech communications with others while using the device.

BRIEF DESCRIPTION OF THE DRAWINGS

FIG. 1 is a schematic illustration of a prior art electrolarynx 100 in use, with the electrolarynx 100 being pressed against a predetermined location on the throat 20 of a patient 10.

FIG. 2A is a schematic illustration of a prior art electrolarynx 100.

FIG. 2B is an exploded view of the prior art electrolarynx 100 as shown in FIG. 2A.

FIG. 3A is a schematic illustration of a preferred embodiment of the electrolarynx 200, in which the radial distance between the coil wires and the inner diameter of non-magnetic cup (denoted by distance "y" or "coil-cup gap" in FIG. 3A) is greater than the radial distance between the outer diameter of the guide disc and the inner diameter of the coil cylinder (denoted by distance "x" or "guide disc gap").

FIG. 3B is an exploded view of the preferred embodiment of the electrolarynx 200 as shown in FIG. 3A.

FIG. 3C is a schematic top view of the locating diaphragm 224 as shown in FIGS. 3A and 3B.

FIG. 4A is a schematic illustration of another preferred embodiment of the electrolarynx 200, without a magnetic cup.

FIG. 4B is an exploded view of the preferred embodiment of the electrolarynx 200 as shown in FIG. 4A.

FIG. 5 is a schematic illustration of yet another embodiment of the electrolarynx 200 that has a slimmer profile.

DETAILED DESCRIPTION

Unless otherwise indicated, all numbers expressing quantities of ingredients, dimensions, reaction conditions, and so forth used in the specification and claims are to be understood as being modified in all instances by the term "about."

In this application and the claims, the use of the singular includes the plural unless specifically stated otherwise. In addition, use of "or" means "and/or" unless stated otherwise. Moreover, the use of the term "including," as well as other forms, such as "includes" and "included," is not limiting. Also, terms such as "element" or "component" encompass both elements and components comprising one unit and elements and components that comprise more than one unit unless specifically stated otherwise.

With reference to FIG. 1, a prior art electrolarynx 100 is shown held against the skin of the throat 20 of patient 10. The electrolarynx is positioned on a "sweet spot" that provides a clearest simulated speaking voice. Because the "sweet spot" may change with time, each individual patient will establish and update predetermined positions along throat 20 over time. In FIG. 1, the electrolarynx 100 is shown in modular schematic form, as comprising housing 104 having cap 108 and control actuators 112a and 112b (collectively, "control actuators 112"). Control actuators 112 may include buttons, dials, switches, touchscreen panels, or any other types of actuators, for turning the device on or off, adjusting the volume of the device, and/or adjusting the pitch frequency of the generated sounds or vibrations. The electrolarynx 100 further comprises motor 120, electronics 160, and power supply 180. The motor 120 is described in greater detail with reference to FIGS. 2-5 below.

The electronics 160 include (but are not limited to) a circuit board, potentiometers, transducers, power amplifiers, and a waveform generator. These components of the electronics control the driving of the motor, including adjusting the volume and pitch frequencies of the generated sounds or vibrations based on the user inputs to the control actuators.

The power supply 180 includes any conventionally known portable source of power, including batteries (e.g., nickel-cadmium batteries, NiMH batteries, Li-ion batteries, watch batteries, etc.), solar cells, and kinetic drives (similar to those used in kinetic wrist-watches), etc., or any combination thereof. Because the electrolarynx is intended to be held in a single hand of the patient, the power supply must be chosen to be relatively light weight.

Referring to FIGS. 2A and 2B, a prior art electrolarynx 100 is shown, except for the electronics 160, the power supply 180, and the remainder of the housing 104 containing the electronics 160 and the power supply 180. As shown in FIG. 2B, the electrolarynx 100 includes cap 108, motor 120, and housing 104 (shown as a cutout). Cap 108 includes contact diaphragm 108a (which would make direct contact with the throat 20 of patient 10, as shown in FIG. 1) and cap sidewalls 108b. Contact diaphragm 108a of cap 108 is made of a resilient, flexible material, such as plastic or rubber, or other suitable non-abrasive, flexible material. Cap 108 and housing 104 is made of a resilient, solid material, such as plastic or metal, or other suitable, rigid material.

Motor 120 comprises bobbin 128 and locating diaphragm 124 having a recess at the center thereof. Bobbin 128 includes support plate 132 having a first side (facing cap 108) and a second side (facing the majority of housing 104), a striker 136 on the first side, and coil support structure 140 on the second side. Striker 136 has a circumferential groove 136a perpendicular to the axis of striker 136 (which is aligned with the axis of the housing, i.e., along the T-axis, as shown in FIG. 2A) in which the recess of locating diaphragm 124 fits, so as to maintain the alignment of bobbin 128 along the axis of the housing (T-axis) when locating diaphragm 124 is fitted onto the end of sidewalls 104b of housing 104. When the device is assembled, striker 136 makes direct contact with contact diaphragm 108a of cap 108. Coil support structure 140 includes coil wires 140a and coil cylinder 140b, around which coil wires 140a are wound.

Motor 120 further comprises magnet 148, guide disc 144, and fastening mechanism 152 (such as a screw), which holds and sandwiches magnet 148 between guide disc 144 and inner surface 104a of housing 104 so that the axis of magnet 148 and guide disc 144 align with the axis (T-axis) of housing 104.

When the electronics send a current, which is modulated by the waveform generator (not shown) and amplified by the power amplifier (not shown), the current in the coil wires 140a creates a magnetic field that interacts with the magnet 148 to cause the bobbin 128 (and thus the striker 136) to oscillate along the axis (T-axis) of the housing 104, thus causing the contact diaphragm 108a (which is in contact with the striker 136) to generate vibrations that simulate those vibrations produced by the larynx.

Motor 120 also comprises magnetic housing 156, which is embodied by a magnetic cup 156 having walls that extend axially (along the T-axis) toward cap 108 of housing 104 so as to surround a substantial, if not the entire, portion of guide disc 144. Magnetic cup 156 may be made of magnetic materials (e.g., a ferro-magnet, etc.). Magnetic cup 156 serves to center coil wires 140a so as to maintain the alignment of striker 136 along the axis (T-axis) of housing 104. By centering striker 136 and coil wires 140a in this manner, a clear tone may be produced and amplified from coil wires 140a, which float in magnetic housing 156. In prior art electrolarynxes 100, as shown in FIGS. 2A and 2B, the radial distance "y" between coil wires 140a and the inner diameter of magnetic cup 156 (i.e., "coil-cup gap" or "cup gap") is less than the radial distance "x" between the outer diameter of guide disc 144 and the inner diameter of coil cylinder 140b (i.e., the "guide disc gap"). This may result in gravitational wear as discussed above. Several approaches to solve this issue of gravitational wear are described below with reference to FIGS. 3A through 5.

With reference to FIGS. 3A-3C, an embodiment of the electrolarynx 200 is shown, except for the electronics 260, the power supply 280, and the remainder of the housing 204 containing the electronics and the power supply.

The electronics 260 (not shown, but similar to electronics 160) include (but are not limited to) a circuit board, potentiometers, transducers, power amplifiers, and a waveform generator. These components of the electronics control the driving of the motor, including adjusting the volume and pitch frequencies of the generated sounds or vibrations based on the user inputs to control actuators 212 (not shown). For example, the waveform generator is configured to generate an input signal of a select frequency. The control actuators 212 (not shown) may include any buttons, dials, switches, and touchscreen panels, etc., that may be used to turn the device on or off, adjust the volume of the device, and/or adjust the pitch frequency of the generated sounds or vibrations.

The power supply 280 (not shown, but similar to power supply 280) includes any conventionally known portable source of power, including batteries (e.g., nickel-cadmium batteries, NiMH batteries, Li-ion batteries, watch batteries, etc.), solar cells, and kinetic drives (similar to those used in kinetic wrist-watches), etc., or any combination thereof. Because the electrolarynx 200 is intended to be held in a single hand of the patient, the power supply 280 must be chosen to be relatively light weight.

With reference to FIG. 3B, the electrolarynx 200 includes cap 208, motor (or transducer) 220, and housing 204 (shown as a cutout). Cap 208 comprises contact diaphragm 208a, sidewalls 208b, and connector end 208c. Housing 204 comprises inner motor housing surface 204a, sidewalls 204b, connector end 204c, and lip 204d. Because contact diaphragm 208a is intended to make direct contact with throat 20 of patient 10 (similar to that shown in FIG. 1), contact diaphragm 208a is preferably made of a resilient, flexible material, such as plastic or rubber, or other suitably non-abrasive, flexible material. Cap 208 and housing 204 are each preferably made of a resilient, solid material, such as plastic or metal, or other suitable, rigid material, so as to protect the motor 220, electronics 206 (not shown), and power supply 280 (not shown) that are housed within.

Motor (or transducer) 220 comprises a coil portion and a magnet portion.

The coil portion of transducer 220 comprises locating diaphragm 224 and bobbin 228. Locating diaphragm 224 comprises diaphragm 224a, sidewalls 224b, connector end 224c, lip 224d, and recess 224e. Bobbin 228 includes support plate 232 extending radially from the housing axis (T-axis). The support plate 232 includes a first side (facing cap 204) and a second side (facing the inner motor housing surface 204a of housing 204). Bobbin 228 further includes striker 236 on the first side of support plate 232, and coil support structure 240 on the second side of support plate 232. Striker 236 has a longitudinal length perpendicular (or normal) to the surface of the first side of support plate 232, and a circumferential groove 236a located perpendicular to the longitudinal length (or axis) of striker 236 and at a predetermined position along the longitudinal length of striker 236. In use, the longitudinal length (or axis) of striker 236 is aligned with the axis of the housing, i.e., along the T-axis, as shown in FIG. 3A. With reference to FIGS. 3B and 3C, recess 224e of locating diaphragm 224 would fit snugly around groove 236a of striker 236, so as to maintain the alignment of bobbin 228, and thus confine striker 236 for movement along the axis of the housing (T-axis) when locating diaphragm 224 is fitted onto an end 204c of housing 204. Although FIG. 3C shows a circular recess 224e that corresponds to cylindrical striker 236, recess 224e may be of any shape that matches the cross-sectional shape of striker 236 (e.g., square, rectangle, triangle, or other polygon).

In some embodiments, the locating diaphragm 224 has sidewalls 224b extending along a sidewall length parallel to the housing axis (T-axis). Locating diaphragm 224 also has an extended lip 224d extending radially inward along the inner circumference of its sidewalls 224b. A corresponding lip (or groove) 204d is provided on the end 204c of housing 204 so that it extends radially outward along the outer circumference of connector end 204c (as shown in FIGS. 3A and 3B). This allows the locating diaphragm 224 to securely attach to housing 204. Alternatively, lip 224d may be positioned anywhere along the inner length of sidewall 224b, and lip 204d may be positioned anywhere along the outer length of sidewall 204b. In other alternative embodiments, complementary threading or a luer-lock type configuration may be used in place of lip 224d and lip 204d.

Likewise, cap 208 may attach to housing 204 via respective connector ends 208c and 204c (as shown, e.g., in FIG. 3A) via any of the lip-type connector, screw-type connector, luer-type connector, or other suitable connector type.

In some embodiments, lip 224d and lip 204d may extend uniformly along the respective inner/outer circumferences of sidewalls 224b and 204b, while in other embodiments, at least one of lip 224d and lip 204d may include a plurality of lip extensions interspersed (i.e., with gaps between adjacent lip extensions) along the respective inner/outer circumferences of sidewalls 224b and 204b. In the embodiments having groove 204d (instead of lip 204d), the groove 204d would be a uniform depression about the outer circumference of the housing 204 at any predetermined position along the housing length, while lip 224d may be uniform or embodied as a plurality of lip extensions (with alternating gaps) along the inner circumference of sidewalls 224b.

As with the prior art electrolarynx 100, as discussed above, when the device is assembled, striker 236 makes direct contact with contact diaphragm 208a of cap 208. Coil support structure 240 includes coil wires 240a and a coil cylinder 240b around which coil wires 240a are wound. Coil wires 240a are electrically coupled to the waveform generator to create an electromagnetic field, and include lead wires (not shown) at either end of the coil that are fed through inner motor housing surface 204a via through-holes to the waveform generator of electronics 260 (not shown) that are housed in housing 204. In some embodiments, grooves positioned along the inner sidewalls 204b of housing 204 (preferably parallel to the T-axis) that allow the lead wires (not shown) to unobtrusively fit within the sidewalls 204b of housing 204.

The magnet portion of transducer 220 comprises magnet 248, guide disc 244, and fastening mechanism 252 (including, but not limited to, a screw), which holds and sandwiches magnet 248 between guide disc 244 and inner motor housing surface 204a of housing 204 so that the axis of magnet 248 and guide disc 244 align with the axis (T-axis) of housing 204.

In use, magnet 248 is configured to interact with the electromagnetic field generated by the coil portion of transducer 220. In particular, the waveform generator is configured to produce, as an input signal, a waveform having alternating positive and negative values so as to generate a dynamic electromagnetic field that alternately attracts and repels the magnet, so as to drive the movement of the bobbin 228 along the housing axis (T-axis). As a result, the guide disc 244 is telescopingly received within the coil cylinder 240b. Here, "telescopingly received" refers to the coil cylinder 240b and the guide disc 244 being in relative motion with each other along the housing axis when in use, similar to sections of a collapsing telescope being in relative motion with each other along the telescope's axis when the telescope is either extended or collapsed.

In some embodiments, such as that shown in FIGS. 3A and 3B, motor 220 also comprises magnetic housing 256, which is embodied by magnetic (or non-magnetic) cup 256 having sidewalls 256b that extend axially (along the T-axis) toward cap 208 of housing 204 so as to surround a substantial, if not the entire, portion of guide disc 244 (as shown, e.g., in FIG. 3A). A magnetic cup 256 may be made of, for example, a ferrous magnet. A non-magnetic cup 256 may be made of non-magnetic materials (including, but not limited to, steel). The magnetic or non-magnetic cup 256, serves to center coil wires 240a so as to maintain the alignment of striker 236 along the axis (T-axis) of housing 204. As with the prior art electrolarynx 100, as discussed above, by centering striker 236 and coil wires 240a in this manner, a clear tone may be produced and amplified from coil wires 240a, which floats in magnetic housing 256.

Referring to FIG. 3A, the uniform radial distance "y'" between coil wires 240a and the inner diameter of sidewall 256b of magnetic or non-magnetic cup 256 defines the "coil-cup gap" or "cup gap." Likewise, the uniform radial distance "x" between the outer diameter of guide disc 244 and the inner diameter of coil cylinder 240b defines the "guide disc gap." Unlike in prior art electrolarynxes 100, as shown in FIGS. 2A and 2B, the "coil-cup gap" or "cup gap" of electrolarynx 200 is greater than the "guide disc gap." In other words, y'>x (as shown in FIG. 3A), where y'>y (as shown in FIGS. 2A and 3A).

To accomplish a greater distance y' or "cup gap," some embodiments include a magnetic or non-magnetic cup 256 that has thinner sidewalls 256b compared to the prior art cup 156 of prior art electrolarynx 100 (the cup 256 may otherwise be of similar dimensions as cup 156). In other embodiments, the thickness of the sidewalls 256b of cup 256 may be similar to, or the same as, that of the walls of cup 156, but the overall diameter of cup 256 may be increased so as to achieve a relatively greater distance y' or "cup gap." By increasing the cup gap y', gravitational wear may be avoided. In some embodiments, the distance y' or "cup gap" y' may be 0.015 inch (or –0.381 mm), or greater.

In another aspect of the disclosure, an embodiment of the electrolarynx 200 is shown in FIGS. 4A and 4B, which differs from the embodiment as shown in FIGS. 3A and 3B only in that magnetic or non-magnetic cup 256 has been eliminated or removed. All other components are the same (compare, e.g., FIGS. 3B and 4B).

In the embodiment as shown in FIGS. 4A and 4B, because locating diaphragm 224 is the sole means of axial alignment of striker 236 with the axis (T-axis) of housing 204, it must be preferably made of a material (such as rubber, etc.) that enables the locating diaphragm 224 to perform this function for a prolonged period. During testing, the inventors discovered that functionality of the electrolarynx 200 is not significantly diminished even without the magnetic or non-magnetic cup 256.

With reference to FIG. 4A, the uniform radial distance "z" between coil wires 240a and the inner diameter of sidewall 204b of housing 204 defines the "coil-housing gap" or "housing gap." As in FIG. 3A, the uniform radial distance "x" between the outer diameter of guide disc 244 and the inner diameter of coil cylinder 240b defines the "guide disc gap." According to a preferred embodiment, an electrolarynx 200 without cup 256 allows for a greater "housing gap," where "z>y'" (compare FIGS. 3A and 4A). In some embodiments, the distance z or "housing gap" z may be 0.015 inch (or –0.381 mm), or greater. Thus, gravitational wear may be avoided.

Referring to FIG. 5, because the cup 256 is eliminated, electrolarynx 200 may be made slimmer in diameter (and in profile). A slimmer profile allows for a less obtrusive device that may foster greater comfort that patients have in communicating with others by speech. Here, the radial distance between coil wires 240a and sidewalls 204b (distance "z'" or "housing gap" as shown in FIG. 5), although smaller than distance "z" or the "housing gap" (as shown in FIG. 4A), is still equal to or greater than distance "y'" or the "cup gap" (as shown in FIG. 3A). Thus, gravitational wear may be avoided. In some embodiments, the distance z' or "housing gap" z' may be 0.015 inch (or –0.381 mm), or greater.

Various embodiments of the disclosure could also include permutations of the various elements recited in the claims as if each dependent claim was multiple dependent claims incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. An electro-larynx comprising:
    a waveform generator configured to generate an input signal of a select frequency;
    a transducer comprising:
    a housing extending along a housing axis;
    a striker confined for movement along the housing axis;
    a bobbin comprising a support plate extending radially from the housing axis with the striker attached to the support plate at the housing axis, the bobbin further comprising a coil cylinder extending axially from the support plate opposite the striker, the coil cylinder being wrapped with a coiled wire electrically coupled to the waveform generator to create an electromagnetic field, an outer surface of the coiled wire being a uniform first distance from an inner surface of the housing in use, said uniform first distance defining a housing gap;

a magnet mounted within the housing, said magnet being configured to interact with the electromagnetic field; and a guide disc telescopingly received within the coil cylinder, an outer surface of the guide disc being a uniform second distance from an inner surface of the coil cylinder, said uniform second distance defining a guide disc gap, wherein the magnet is sandwiched between the guide disc and the housing, wherein the housing gap is greater than the guide disc gap.

2. The electro-larynx of claim 1, wherein the transducer further comprises a locating diaphragm that confines the striker to movement along the housing axis.

3. The electro-larynx of claim 2, wherein the striker, which has a longitudinal length parallel with the housing axis, has a circumferential groove at a predetermined position along the longitudinal length, wherein the locating diaphragm has a recess that is confined to movement along the housing axis, wherein the recess fits about the circumferential groove so as to confine the striker to movement along the housing axis.

4. The electro-larynx of claim 2, wherein the locating diaphragm includes sidewalls extending along a sidewall length parallel to the housing axis, said sidewalls being configured to attach to the housing.

5. The electro-larynx of claim 4, wherein the sidewalls include a lip extending radially toward the housing axis, said lip engaging with the housing.

6. The electro-larynx of claim 5, wherein the lip is a uniformly circumferential extension positioned at an end of the side wall axially distant from the recess.

7. The electro-larynx of claim 5, wherein the lip is a uniformly circumferential extension positioned at a predetermined position along the sidewall length.

8. The electro-larynx of claim 4, wherein the housing includes at least one of a housing lip and a housing groove positioned at a predetermined position along a housing length parallel with the housing axis, said at least one of the housing lip and the housing groove extending about an outer circumference of the housing, wherein said at least one of the housing lip and the housing groove is configured to engage with an inner circumference of the sidewalls of the locating diaphragm so as to allow the locating diaphragm to be attached to the housing.

9. The electro-larynx of claim 8, wherein said housing lip is a uniform protrusion about the outer circumference of the housing at the predetermined position along the housing length, wherein said housing groove is a uniform depression about the outer circumference of the housing at the predetermined position along the housing length.

10. The electro-larynx of claim 2, wherein the locating diaphragm is made of a material including rubber.

11. The electro-larynx of claim 1, wherein the housing gap is at least 0.015 inch.

12. The electro-larynx of claim 1, further comprising a cup-shaped magnetic housing located within the housing, said magnetic housing having cup sidewalls extending axially, parallel with the housing axis, said cup sidewalls being configured to surround at least a portion of the guide disc when in use, an inner diameter of the cup sidewalls being a uniform third distance from the outer surface of the guide disc, said uniform third distance defining a cup gap, wherein the cup gap is greater than the guide disc gap.

13. The electro-larynx of claim 12, wherein the magnetic housing includes one of a magnetic cup and a non-magnetic cup.

14. The electro-larynx of claim 12, wherein the cup gap is at least 0.015 inch.

15. A method of extending the life of an electrolarynx, the method comprising:
providing an electrolarynx comprising:
a waveform generator configured to generate an input signal of a select frequency;
a transducer comprising:
a housing extending along a housing axis;
a striker;
a bobbin comprising a support plate extending radially from the housing axis with the striker attached to the support plate at the housing axis, the bobbin further comprising a coil cylinder extending axially from the support plate opposite the striker, the coil cylinder being wrapped with a coiled wire electrically coupled to the waveform generator to create an electromagnetic field, an outer surface of the coiled wire being a uniform first distance from an inner surface of the housing in use, said uniform first distance defining a housing gap;
a magnet mounted within the housing, said magnet being configured to interact with the electromagnetic field; and
a guide disc telescopingly received within the coil cylinder, an outer surface of the guide disc being a uniform second distance from an inner surface of the coil cylinder, said uniform second distance defining a guide disc gap, wherein the magnet is sandwiched between the guide disc and the housing; and
providing a housing gap greater than a guide disc gap.

16. The method of claim 15, wherein providing a housing gap greater than a guide disc gap includes providing a housing gap that is at least 0.015 inch.

17. The method of claim 15, further comprising:
providing a locating diaphragm that confines the striker to movement along the housing axis.

18. A method of extending the life of an electrolarynx, the method comprising:
providing an electrolarynx comprising:
a waveform generator configured to generate an input signal of a select frequency;
a transducer comprising:
a housing extending along a housing axis;
a striker;
a bobbin comprising a support plate extending radially from the housing axis with the striker attached to the support plate at the housing axis, the bobbin further comprising a coil cylinder extending axially from the support plate opposite the striker, the coil cylinder being wrapped with a coiled wire electrically coupled to the waveform generator to create an electromagnetic field;
a cup-shaped magnetic housing located within the housing, said magnetic housing having cup sidewalls extending axially, parallel with the housing axis, said cup sidewalls being configured to surround at least a portion of the guide disc when in use, an inner diameter of the cup sidewalls being a uniform first distance from the outer surface of the guide disc, said uniform first distance defining a cup gap
a magnet mounted within the magnetic housing, said magnet being configured to interact with the electromagnetic field; and
a guide disc telescopingly received within the coil cylinder, an outer surface of the guide disc being a uniform second distance from an inner surface of the coil cylinder, said uniform second distance defining a guide disc gap, wherein the magnet is sandwiched between the guide disc and the housing;

providing the cup gap greater than the guide disc gap.

19. The method of claim 18, wherein providing a cup gap greater than a guide disc gap includes providing a cup gap that is at least 0.015 inch.

* * * * *